United States Patent
Pettersen et al.

(10) Patent No.: US 11,149,029 B2
(45) Date of Patent: Oct. 19, 2021

(54) SALTS OF IJAK INHIBITORS AND METHODS OF USING THE SAME

(71) Applicant: AstraZeneca AB, Södertälje (SE)

(72) Inventors: Anna Matilda Angelica Pettersen, Gothenburg (SE); James McCabe, Macclesfield (GB); Carl-Johan Aurell, Gothenburg (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 16/513,781

(22) Filed: Jul. 17, 2019

(65) Prior Publication Data

US 2020/0062737 A1 Feb. 27, 2020

Related U.S. Application Data

(60) Provisional application No. 62/866,013, filed on Jun. 25, 2019, provisional application No. 62/699,955, filed on Jul. 18, 2018.

(51) Int. Cl.
| | |
|---|---|
| *C07D 403/14* | (2006.01) |
| *C07D 403/04* | (2006.01) |
| *A61K 31/506* | (2006.01) |
| *A61P 11/06* | (2006.01) |

(52) U.S. Cl.
CPC .......... *C07D 403/14* (2013.01); *A61K 31/506* (2013.01); *A61P 11/06* (2018.01); *C07D 403/04* (2013.01)

(58) Field of Classification Search
CPC ...... C07D 403/04; A61K 31/506; A61P 11/06
See application file for complete search history.

(56) References Cited

FOREIGN PATENT DOCUMENTS

| | | |
|---|---|---|
| WO | 2017050938 A1 | 3/2017 |
| WO | 2018134213 A1 | 7/2018 |

OTHER PUBLICATIONS

Simone, Oncology: Introduction, Cecil Textbook of Medicine, 20th Edition, vol. 1, pp. 1004-1010, 1996.*
Gura, Systems for identifying New Drugs Are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*
Pearce et al., Failure modes in anticancer drug discovery and development, Cancer Drug Design and Discovery Edited by Stephen Neidle, Chapter 18, pp. 424-435 (2008).*
Acute Leukemia, Merck Manual (Online Edition) 6 pages, pp. 1-6 (2013).*
International Search Report and Written Opinion for PCT/EP2019/069252, dated Oct. 1, 2019.

* cited by examiner

*Primary Examiner* — Deepak R Rao

(57) ABSTRACT

The present disclosure relates to salts of compounds of Formula (I) prepared as a xinafoate (1-hydroxy-2-naphthoate) salt (Formula (Ia)), pharmaceutically acceptable compositions comprising same and methods of using the same.

Formula (Ia)

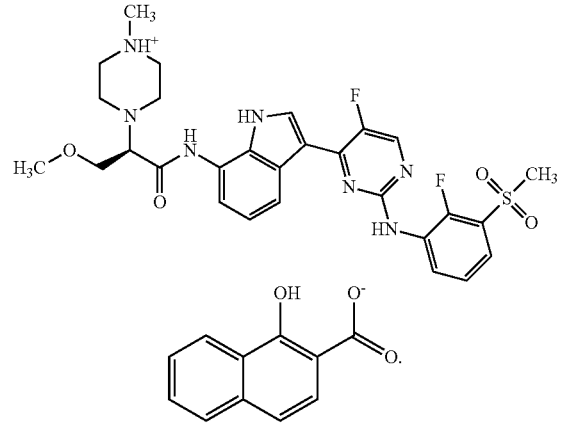

12 Claims, 1 Drawing Sheet

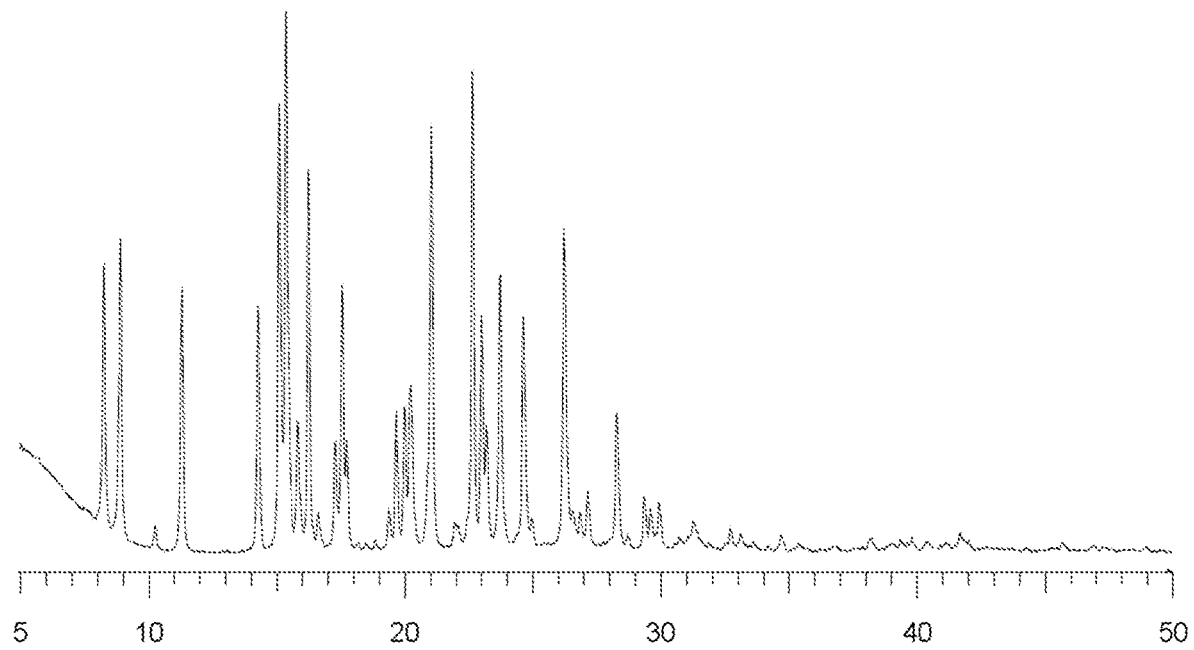

SALTS OF IJAK INHIBITORS AND METHODS OF USING THE SAME

BACKGROUND

The novel salts of Formula (I) of the present disclosure are expected to be useful for the treatment or prophylaxis of conditions mediated alone or in part by JAnus Kinases (or JAK) which are a family of cytoplasmic protein tyrosine kinases including JAK1, JAK2, JAK3 and TYK2. Each of the JAK kinases is selective for the receptors of certain cytokines, though multiple JAK kinases can be affected by particular cytokine or signaling pathways. Studies suggest that JAK3 associates with the common gamma chain (γc) of the various cytokine receptors. In particular, JAK3 selectively binds to receptors and is part of the cytokine signalling pathway for IL-2, IL-4, IL-7, IL-9, IL-15 and IL-21. The kinase JAK1 interacts with, among others, the receptors for cytokines IL-2, IL-4, IL-7, IL-9 and IL-21. Upon the binding of certain cytokines to their receptors (e.g., IL-2, IL-4, IL-7, IL-9, IL-15 and IL-21), receptor oligomerization occurs, resulting in the cytoplasmic tails of associated JAK kinases being brought into proximity and facilitating the trans-phosphorylation of tyrosine residues on the JAK kinase. This trans-phosphorylation results in the activation of the JAK kinase.

Phosphorylated JAK kinases bind various Signal Transducer and Activator of Transcription (STAT) proteins. These STAT proteins, which are DNA binding proteins activated by phosphorylation of tyrosine residues, function both as signalling molecules and transcription factors and ultimately bind to specific DNA sequences present in the promoters of cytokine-responsive genes (Leonard et al., (2000), *J. Allergy Clin. Immunol.* 105:877-888). Signalling of JAK/STAT has been implicated in the mediation of many abnormal immune responses such as allergies, asthma, autoimmune diseases such as transplant (allograft) rejection, rheumatoid arthritis, amyotrophic lateral sclerosis and multiple sclerosis, as well as in solid and hematologic malignancies such as leukemia and lymphomas. For a review of the pharmaceutical intervention of the JAK/STAT pathway see Frank, (1999), *Mol. Med.* 5:432:456 and Seidel et al., (2000), *Oncogene* 19:2645-2656 and Vijayakriishnan et al, *Trends Pharmacol. Sci* 2011, 32, 25-34 and Flanagan et al, *J. Med. Chem.* 2014, 57, 5023-5038.

Given the importance of JAK kinases compounds which modulate the JAK pathway can be useful for treating diseases or conditions where the function of lymphocytes, macrophages, or mast cells is involved (Kudlacz et al., (2004) *Am. J. Transplant* 4:51-57; Changelian (2003) *Science* 302:875-878). Conditions in which targeting of the JAK pathway or modulation of the JAK kinases are contemplated to be therapeutically useful include, leukemia, lymphoma, transplant rejection (e.g., pancreas islet transplant rejection, bone marrow transplant applications (e.g., graft-versus-host disease), autoimmune diseases (e.g., diabetes), and inflammation (e.g., asthma, allergic reactions).

In view of the numerous conditions that are contemplated to benefit by treatment involving modulation of the JAK pathway, it is apparent that new compounds and new forms of compounds that modulate JAK pathways and methods of using these compounds should provide substantial therapeutic benefits to a wide variety of patients.

SUMMARY

The present disclosure relates to novel salts of Formula (I):

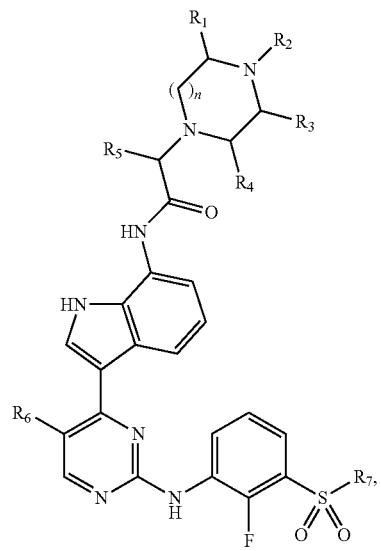

Formula (I)

pharmaceutical compositions containing salts of Formula (I), and methods of using the same.

Compounds of Formula (I) are described in International Patent Application PCT/EP2018/051038, disclosing a genus of JAK inhibiting compounds and including (R)—N-(3-(5-fluoro-2-((2-fluoro-3-(methylsulfonyl)phenyl)amino)pyrimidin-4-yl)-1H-indol-7-yl)-3-methoxy-2-(4-methylpiperazin-1-yl)propanamide—see Example 35. International Patent Application PCT/EP2018/051038 describes additional JAK inhibiting compounds, including various salts of (R)—N-(3-(5-fluoro-2-((2-fluoro-3-(methylsulfonyl)phenyl)amino)pyrimidin-4-yl)-1H-indol-7-yl)-3-methoxy-2-(4-methylpiperazin-1-yl)propanamide.

Disclosed herein are compounds of Formula (I) prepared as novel salts that are useful in the treatment of conditions in which targeting of the JAK pathway or inhibition of JAK kinases, particularly JAK1.

In at least one embodiment, the present disclosure includes compounds of Formula (I) prepared as a xinafoate (1-hydroxy-2-naphthoate) salt (Formula (Ia)):

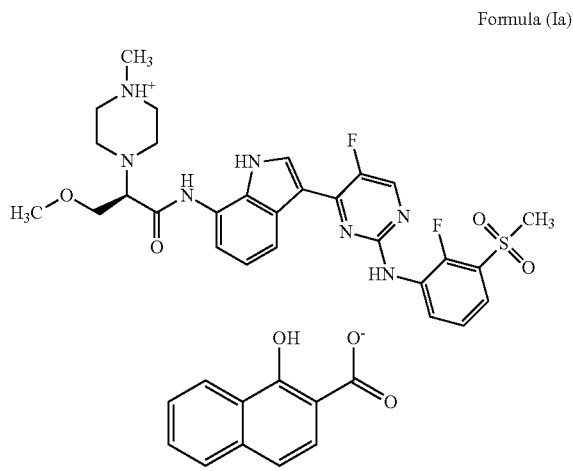

Formula (Ia)

4-{(2R)-1-[(3-{5-fluoro-2-[2-fluoro-3-(methanesulfonyl) anilino]pyrimidin-4-yl}-1H-indol-7-yl)amino]-3- methoxy-1-oxopropan-2-yl}-1-methylpiperazin-1-ium; 1-hydroxynaphthalene-2-carboxylate The xinafoate salt of the present disclosure has a xinafoic acid stoichiometry of 1:1 (as shown above). Also disclosed herein is a process for preparing the xinafoate salt of Formula (Ia). Further disclosed are pharmaceutical compositions comprising a xinafoate salt of Formula (Ia), and a pharmaceutically acceptable diluent, excipient or carrier. In another embodiment, disclosed are methods of treating a JAK-related disorder in a subject in need thereof comprising administering to the subject an effective amount of a xinafoate salt of Formula (Ia). In another embodiment, disclosed is a xinafoate salt of Formula (Ia) for use in treating a JAK-related disorder. In another embodiment, disclosed are pharmaceutical compositions comprising a xinafoate salt of Formula (Ia) for use in treating a JAK-related disorder. In another embodiment, disclosed is the use of a xinafoate salt of Formula (Ia) in the manufacture of a medicament for treating a JAK-related disorder. Also disclosed is a novel process for preparing the xinafoate salt of Formula (Ia) and two novel intermediates:

4-[(1R)-1-carboxy-2-methoxyethyl]-1-methylpiperazin-1-ium (2R,3R)-3-carboxy-2,3-dihydroxypropanoate hydrate (1:1:2), as illustrated below:

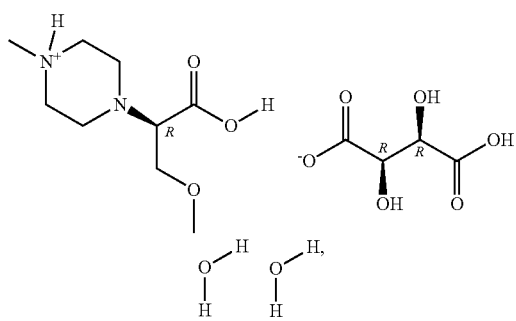

and
1-[(1R)-1-carboxy-2-methoxyethyl]-4-methylpiperazine-1,4-diium dichloride, as illustrated below:

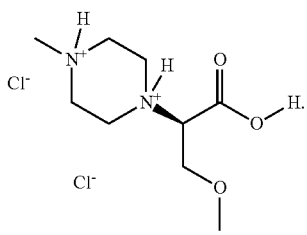

DESCRIPTION OF FIGURES

FIG. 1 shows an X-ray powder diffraction pattern (XRPD) for 4-{(2R)-1-[(3-{5-fluoro-2-[2-fluoro-3-(methanesulfonyl)anilino]pyrimidin-4-yl}-1H-indol-7-yl)amino]-3-methoxy-1-oxopropan-2-yl}-1-methylpiperazin-1-ium; 1-hydroxynaphthalene-2-carboxylate.

DETAILED DESCRIPTION

In some embodiments, disclosed are solid forms of the compounds of Formula (I) and (Ia). The term "solid form" includes polymorphs, crystalline salts, solvates, hydrates and amorphous forms of the compounds of Formula (I) and (Ia). According to at least one embodiment of the present disclosure, the salts of the present disclosure are crystalline. The salts may also exist in solvated as well as unsolvated forms such as, for example, hydrated forms. It is to be understood that the present disclosure encompasses all such solvated and unsolvated forms of compounds of Formula (I). The term "solvate" includes crystalline structures of the same chemical material, but incorporating molecules of solvent within the molecular packing of the crystalline structure. The term "hydrates" includes crystalline structures of the same chemical material, but incorporating molecules of water within the molecular packing of the crystalline structure.

Compounds can exist as different crystal structure forms known as polymorphs. As used herein, "polymorph" is understood to mean a crystalline form having the same chemical composition but different spatial arrangement of the molecules, atoms, and/or ions forming the crystal. Although polymorphs have the same chemical composition, the may have different geometrical arrangement and therefore may exhibit different physical properties such as density, hardness, melting point, flexibility, durability, stability, dissolution, etc.

It is generally known that solid materials may be characterized using conventional techniques such as X-Ray Powder Diffraction (XRPD), Differential Scanning Calorimetry (DSC), Thermal Gravimetric Analysis (TGA), Diffuse Reflectance Infrared Fourier Transform (DRIFT) spectroscopy, Near Infrared (NIR) spectroscopy, solution and/or solid state nuclear magnetic resonance spectroscopy. The water content of such solid materials may be determined by Karl Fischer analysis.

The solid forms described herein provide XRPD patterns substantially the same as the XRPD patterns shown in the FIGURES, and have the various 2-theta (2θ) values as shown in the Tables included herein. One skilled in the art will understand that an XRPD pattern or diffractogram may be obtained which has one or more measurement errors depending on the recording conditions, such as the equipment or machine used. Similarly, it is generally known that intensities in an XRPD pattern may fluctuate depending on measurement conditions or sample preparation as a result of preferred orientation. Persons skilled in the art of XRPD will further realize that the relative intensity of peaks can also be affected by, for example, grains above 30 µm in size and non-unitary aspect ratios. The skilled person understands that the position of reflections can be affected by the precise height at which the sample sits in the diffractometer, and also the zero calibration of the diffractometer. The surface planarity of the sample may also have a small effect.

Because of these considerations, the diffraction pattern data presented are not to be taken as absolute values (Jenkins, R & Snyder, R. L. 'Introduction to X-Ray Powder Diffractometry' John Wiley & Sons 1996; Bunn, C. W. (1948), 'Chemical Crystallography', Clarendon Press, London; Klug, H. P. & Alexander, L. E. (1974), 'X-Ray Diffraction Procedures'). It should also be understood that the solid forms embodied herein are not limited to those that provide XRPD patterns that are identical to the XRPD pattern shown in the FIGURES, and any solid forms providing XRPD patterns substantially the same as those shown in the FIGURES fall within the scope of the corresponding embodiment. A person skilled in the art of XRPD can judge the substantial identity of XRPD patterns. Generally, a measurement error of a diffraction angle in an XRPD is approximately 2θ (+0.2°), and such degree of a measurement error should be considered when analysing the X-ray powder diffraction pattern in the FIGURES and when reading data contained in the Tables included herein.

Form A

In at least one embodiment, disclosed is Form A, a xinafoate salt of 4-{(2R)-1-[(3-{5-fluoro-2-[2-fluoro-3-(methanesulfonyl)anilino]pyrimidin-4-yl}-1H-indol-7-yl)amino]-3-methoxy-1-oxopropan-2-yl}-1-methylpiperazin-1-ium; 1-hydroxynaphthalene-2-carboxylate.

In some embodiments, Form A is characterised in that it provides an X-ray powder diffraction (XRPD) pattern substantially as shown in FIG. 1.

In some embodiments, Form A has an XRPD pattern comprising at least one peak expressed as 2-theta (+2°) selected from the peaks listed in Table 1. It will be understood that the 2-theta values of the X-ray powder diffraction pattern may vary slightly from one machine to another or from one sample to another, and so the values quoted are not to be construed as absolute.

In some embodiments, Form A is characterised in providing at least one of the following 2θ values measured using CuKα radiation: 15.00 and 21.0° and 22.60°.

In some embodiments, Form A is characterised in providing at least one of the following 2θ values measured using CuKα radiation: 8.2, 8.9, 11.2, 14.2, 15.0, 15.3, 16.2, 17.5, 21.0, 22.6, 23.0, 23.7, 24.6 and 26.2°.

In some embodiments, the degree of crystallinity of Form A is greater than about 60%, for example, greater than about 80%, such as greater than about 90% and, in at least one embodiment, greater than about 95%. In yet another embodiment, the degree of crystallinity is greater than about 98%.

According to a further aspect of the present disclosure there is provided a process for the preparation of Form A, comprising:
 (i) Dissolving 5-((5-methyl-2-((3,4,5-trimethylphenyl)amino)pyrimidin-4-yl)amino)-benzo[d]oxazol-2(3H)-one free base in a suitable solvent, such as DMSO;
 (ii) Dissolving xinafoate acid in a suitable solvent, such as DMSO;
 (iii) Mixing the two solutions;
 (iv) Optionally adding seed crystals of the xinafoate salt of 5-((5-methyl-2-((3,4,5-trimethylphenyl)amino)pyrimidin-4-yl)amino)-benzo[d]oxazol-2(3H)-one;
 (v) Crystallising the xinafoate salt of 5-((5-methyl-2-((3,4,5-trimethylphenyl)amino)pyrimidin-4-yl)amino)-benzo[d]oxazol-2(3H)-one; and
 (vi) Isolating the xinafoate salt of 5-((5-methyl-2-((3,4,5-trimethylphenyl)amino)pyrimidin-4-yl)amino)-benzo[d]oxazol-2(3H)-one.

According to a further aspect of the present disclosure there is provided a process for the preparation of the two novel intermediates 4-[(1R)-1-carboxy-2-methoxyethyl]-1-methylpiperazin-1-ium (2R,3R)-3-carboxy-2,3-dihydroxypropanoate hydrate (1:1:2) and 1-[(1R)-1-carboxy-2-methoxyethyl]-4-methylpiperazine-1,4-diium dichloride, comprising:
 (i) Dissolving lithium 3-methoxy-2-(4-methylpiperazin-1-yl) propanoate in distilled water at pH 4;
 (ii) Dissolving L-(+)-Tartaric acid in distilled water;
 (iii) Mixing the two solutions from step (i) and step (ii) in a suitable solvent, such as ethanol, to induce crystallization;
 (iv) Stirring the mixture of step (iii) for 20 hours at room temperature;
 (v) Adding suitable solvent to the mixture of step (iv), such as ethanol, and cooling prior to filtration to yield the product 4-[(1R)-1-carboxy-2-methoxyethyl]-1-methylpiperazin-1-ium (2R,3R)-3-carboxy-2,3-dihydroxypropanoate hydrate (1:1:2);
 (vi) Collecting the product of step (v) and drying for 72 hours at reduced pressure;
 (vii) Dissolving the product of step (vi) in distilled water;
 (viii) Performing cationic ion exchange to the product of step (vii); and
 (ix) Eluting the product of step (viii) with 2M HCl and evaporating that solution to dryness which induces crystallization of 1-[(1R)-1-carboxy-2-methoxyethyl]-4-methylpiperazine-1,4-diium dichloride.

Pharmaceutical Compositions & Methods of Use

The novel salts herein may be administered by inhalation as micronised solid particles without any additional excipients, diluents or carriers. In at least one embodiment, pharmaceutical compositions comprising Form A in association with a pharmaceutically-acceptable diluent or carrier are disclosed.

The compositions of the disclosure may be in a form suitable for administration by inhalation (for example as a finely divided powder or a liquid aerosol) or for administration by insufflation (for example as a finely divided powder) using a suitable device.

The compositions of the disclosure may be obtained by conventional procedures using conventional pharmaceutical excipients well known in the art. For instance, compositions intended for inhalation may contain, for example, micronized lactose or other suitable excipients, in an amount up to about 90 w/w % of the composition.

If required, the novel salts may be milled or micronized prior to formulation to provide a uniform particle size distribution. For example, Form A may be milled to provide an average particle size of about 1 μm to 3 μm. Suitable milling and micronisation methods are well known. (Midoux et al., (1999), *Powder Technology*, 104:113-120).

Form A of the present disclosure is expected to be useful in the treatment of diseases or medical conditions mediated alone or in part by JAK, particularly JAK1, i.e. Form A may be used to produce a JAK-inhibitory effect in a warm-blooded animal in need of such treatment. For instance, Form A of the present disclosure can be used to inhibit JAK kinases in vivo as a therapeutic approach towards the treatment or prevention of diseases mediated, either wholly or in part, by a JAK kinase activity (referred to herein as "JAK kinase mediated diseases"). Non-limiting examples of JAK kinase mediated diseases that can be treated or prevented include the treatment of obstructive, restrictive or inflammatory airways diseases of whatever type, etiology, or pathogenesis, in particular an obstructive, restrictive or inflammatory airways disease, including, as mentioned above, asthma, in particular atopic asthma, allergic asthma, non-atopic asthma, bronchial asthma, non-allergic asthma, emphysematous asthma, exercise-induced asthma, emotion-induced asthma, extrinsic asthma caused by environmental factors, infective asthma associated with bacterial, fungal, protozoal and/or viral infection, bronchiolitis, cough variant asthma, drug induced asthma, and the like, rhinitis or sinusitis of different etiologies, including without limitation, seasonal allergic rhinitis, perennial allergic rhinitis, vasomotor rhinitis, sinusitis, including acute, chronic, ethmoid, frontal maxillary or sphenoid sinusitis; chronic obstructive pulmonary disease (COPD), chronic obstructive lung disease (COLD), chronic obstructive airways disease (COAD) or small airways obstruction, including, without limitation, chronic bronchitis, pulmonary emphysema, bronchiectasis, cystic fibrosis, bronchiolitis obliterans; bronchitis, including in particular, acute bronchitis, acute laryngotracheal bronchitis, chronic bronchitis, dry bronchitis, productive bronchitis, infectious asthmatic bronchitis, *Staphylococcus* or streptococcal bronchitis and vesicular bronchitis.

Accordingly, in one aspect of the present disclosure, disclosed are methods of treating JAK kinase mediated diseases in a subject in need thereof, comprising administering to the subject an effective amount of a xinafoate salt of a compound of Formula (Ia) or an effective amount of Form A. Also disclosed are methods of treating JAK kinase mediated diseases in a subject in need thereof, comprising administering to the subject a pharmaceutically acceptable composition comprising an effective amount of a compound of Formula (Ia) or an effective amount of Form A.

In one aspect, also disclosed is a xinafoate salt of a compound of Formula (Ia), for use in treating JAK kinase mediated diseases in a subject in need thereof. In another aspect, disclosed are pharmaceutically acceptable compositions comprising a xinafoate salt of a compound of Formula (Ia), for use in treating JAK kinase mediated diseases in a subject in need thereof. In one aspect, also disclosed is Form A, for use in treating JAK kinase mediated diseases in a subject in need thereof. In another aspect, disclosed are pharmaceutically acceptable compositions comprising Form A, for use in treating JAK kinase mediated diseases in a subject in need thereof.

In one aspect, also disclosed is the use of a xinafoate salt of a compound of Formula (Ia), in the manufacture of a medicament for use in treating JAK kinase mediated diseases in a subject in need thereof. In one aspect, also disclosed is the use Form A, in the manufacture of a medicament for use in treating JAK kinase mediated diseases in a subject in need thereof.

In one aspect of the present disclosure, disclosed are methods of treating asthma in a subject in need thereof, comprising administering to the subject an effective amount of a xinafoate salt of a compound of Formula (Ia) or an effective amount of Form A. Also disclosed are methods of treating asthma in a subject in need thereof, comprising administering to the subject a pharmaceutically acceptable composition comprising an effective amount of a xinafoate salt of a compound of Formula (Ia) or an effective amount of Form A.

In one aspect, also disclosed is a xinafoate salt of a compound of Formula (Ia), for use in treating asthma in a subject in need thereof. In another aspect, disclosed are pharmaceutically acceptable compositions comprising a xinafoate salt of a compound of Formula (Ia) for use in treating asthma in a subject in need thereof. In one aspect, also disclosed is Form A, for use in treating asthma in a subject in need thereof. In another aspect, disclosed are pharmaceutically acceptable compositions comprising Form A for use in treating asthma in a subject in need thereof.

In one aspect, also disclosed is the use of a xinafoate salt of a compound of Formula (Ia), in the manufacture of a medicament for use in treating asthma in a subject in need thereof. In one aspect, also disclosed is the use of Form A, in the manufacture of a medicament for use in treating asthma in a subject in need thereof.

Accordingly, in one aspect of the present disclosure, disclosed are methods of treating COPD in a subject in need thereof, comprising administering to the subject an effective amount of a xinafoate salt of a compound of Formula (Ia), or an effective amount of Form A. Also disclosed are methods of treating COPD in a subject in need thereof, comprising administering to the subject a pharmaceutically acceptable composition comprising an effective amount of a xinafoate salt of a compound of Formula (Ia), or an effective amount of Form A.

In one aspect, also disclosed is a xinafoate salt of a compound of Formula (Ia), for use in treating COPD in a subject in need thereof. In another aspect, disclosed are pharmaceutically acceptable compositions comprising a xinafoate salt of a compound of Formula (Ia) for use in treating COPD in a subject in need thereof. In one aspect, also disclosed is Form A, for use in treating COPD in a subject in need thereof. In another aspect, disclosed are pharmaceutically acceptable compositions comprising Form A for use in treating COPD in a subject in need thereof.

In one aspect, also disclosed is the use of a xinafoate salt of a compound of Formula (Ia), in the manufacture of a medicament for use in treating COPD in a subject in need thereof. In one aspect, also disclosed is the use of Form A, in the manufacture of a medicament for use in treating COPD in a subject in need thereof.

EXAMPLES

The disclosure is further illustrated by way of the following examples, which are intended to elaborate several embodiments of the disclosure. These Examples are not intended to, nor are they to be construed to, limit the scope of the disclosure. It will be clear that the disclosure may be practised otherwise than as particularly described herein. Numerous modifications and variations of the present disclosure are possible in view of the teachings herein and, therefore, are within the scope of the disclosure.

We have found that the novel salts of Formula (I) have favourable properties compared to compounds of Formula (I) free base, for instance. For example, the xinafoate salt has favourable mechanical and physiochemical properties (i.e. non-hygroscopic).

In the Examples, unless otherwise stated:

(i) yields are given for illustration only and are not necessarily the maximum attainable;

(ii) when given, NMR data is in the form of delta values for major diagnostic protons, given in parts per million (ppm) using perdeuterio dimethyl sulfoxide (DMSO-$d_6$) as solvent unless otherwise indicated; the following abbreviations have been used: s, singlet; d, doublet; t, triplet; q, quartet; m, multiplet; br, broad;

(iii) chemical symbols have their usual meanings; SI units and symbols are used;

(iv) solvent ratios are given in volume:volume (v/v) terms;

(v) X-Ray Powder Diffraction analysis was carried out as described in the Examples.

(vi) in the Examples given below the number of moles and the yield stated refer to the raw materials and reagents at 100% w/w, thereby taking account of the purity of the materials used.

Example 1

Intermediate 1: 7-nitro-3-(4,4,5,5-tetramethyl-1,3,2-dioxaborolan-2-yl)-1-tosyl-1H-indole Step 1

A solution of NaOH (599 g, 14986.55 mmol) in water (1500 mL) was added to a stirred mixture of 7-nitro-1H- indole (243 g, 1498.65 mmol) and tetrabutylammonium hydrogen sulfate (50.9 g, 149.87 mmol) in DCM (3000 mL) at 25° C., over a period of 5 minutes under air. The resulting mixture was stirred at 25° C. for 20 minutes. 4-methylphenylsulfonyl chloride (371 g, 1948.25 mmol) was added under air and the resulting mixture was stirred at 25° C. for 16 hours. The reaction mixture was diluted with DCM (2000 mL), and washed sequentially with water (2×500 mL), 10% aqueous $K_2CO_3$ (2×500 mL), and 1 M HCl (2×500 mL) and saturated NaCl (2×500 mL). The organic layer was dried over $Na_2SO_4$, filtered and evaporated. When approximately 200 mL DCM was left, EtOAc (500 mL) was added. The solvent was removed under reduced pressure. When approximately 200 mL EtOAc was left, MTBE (1000 mL) was added. The precipitate was collected by filtration, washed with MTBE (1000 mL) and dried under vacuum to afford 7-nitro-1-tosyl-1H-indole (402 g, 85%) as a white solid.

$^1$H NMR (300 MHz, DMSO-$d_6$) δ 2.39 (s, 3H), 7.09 (d, 1H), 7.40-7.55 (m, 3H), 7.75-7.85 (m, 3H), 7.95-8.00 (m, 1H), 8.06 (d, 1H). m/z (ES+), [M+H]$^+$=317.

Step 2

Bromine (81 mL, 1580 mmol) was added dropwise to 7-nitro-1-tosyl-1H-indole (50 g, 158 mmol) in CCl$_4$ (1000 mL) at 80° C. The resulting solution was stirred at 80° C. for 6 hours. The mixture was cooled to room temperature, concentrated in vacuo and the residue was washed with EtOAc to afford 3-bromo-7-nitro-1-tosyl-1H-indole (53 g, 85%) as a brown solid. $^1$H NMR (300 MHz, DMSO-$d_6$) δ 2.41 (s, 3H), 7.55-7.62 (m, 2H), 7.57 (t, 1H), 7.85-7.92 (m, 3H), 7.96 (d, 1H), 8.49 (s, 1H).

m/z (ES–), [M–H]$^+$=393.

Step 3

A solution 3-bromo-7-nitro-1-tosyl-1H-indole (200 g, 506 mmol), 4,4,4',4',5,5,5',5'-octamethyl-2,2'-bi(1,3,2-dioxaborolane) (193 g, 759 mmol), potassium acetate (99 g, 1012 mmol) and PdCl$_2$(dppf) (18.5 g, 25.3 mmol) in 1,4-dioxane (1500 mL) was degassed with nitrogen three times and the reaction mixture stirred at 90° C. for 8 hours. The mixture was cooled to room temperature and concentrated in vacuo. The solid was treated with water, filtered, washed with methanol and dried in vacuo to afford 7-nitro-3-(4,4,5,5-tetramethyl-1,3,2-dioxaborolan-2-yl)-1-tosyl-1H-indole (150 g, 67%) as a grey solid. $^1$H NMR (400 MHz, CDCl$_3$) δ 1.41 (s, 12H), 2.47 (s, 3H), 7.38-7.43 (m, 3H), 7.66 (d, 1H), 7.87 (d, 2H), 8.24 (s, 1H), 8.29-8.32 (d, 1H). m/z (ES+), [M+H]$^+$=443.

Intermediate 2: 2-fluoro-3-(methylsulfonyl)aniline

Step 1

Copper(I) iodide (1.002 g, 5.26 mmol) was added in one portion to 3-bromo-2-fluoroaniline (5 g, 26.31 mmol), N1,N2-dimethylethane-1,2-diamine (0.464 g, 5.26 mmol) and sodium iodide (7.89 g, 52.63 mmol) in 1,4-dioxane (10 mL) at 25° C. over a period of 1 minute under nitrogen. The resulting suspension was stirred at 110° C. for 1 day. The reaction mixture was filtered through celite and concentrated in vacuo. The crude product was purified by flash silica chromatography using a gradient 5-30% EtOAc in petroleum ether as mobile phase. Pure fractions were evaporated in vacuo to afford 2-fluoro-3-iodoaniline (5.00 g, 80%) as a brown oil.

$^1$H NMR (400 MHz, DMSO-$d_6$) δ 5.32 (bs, 2H), 6.59-6.83 (m, 2H), 6.83-6.93 (m, 1H). m/z (ES+), [M+H]$^+$=238.

Step 2

Copper(I) iodide (0.402 g, 2.11 mmol) was added to 2-fluoro-3-iodoaniline (5.00 g, 21.10 mmol), sodium methanesulfinate (3.23 g, 31.64 mmol), N1,N2-dimethylethane-1,2-diamine (0.558 g, 6.33 mmol) in DMSO (20 mL) under nitrogen. The resulting suspension was stirred at 95° C. for 18 hours. The reaction mixture was diluted with EtOAc (50 mL), washed with water (50 mL) and brine (50 mL). The organic layer was dried over $Na_2SO_4$, filtered and evaporated in vacuo. The residue was purified by preparative TLC using EtOAc/petroleum ether 1:1 to afford 2-fluoro-3-(methylsulfonyl)aniline (3.20 g, 80%) as a colourless oil which solidified on standing.

$^1$H NMR (400 MHz, CDCl$_3$) δ 3.20 (s, 3H), 3.96 (bs, 2H), 6.97-7.13 (m, 2H), 7.20-7.31 (m, 1H). m/z (ES+), [M+H]$^+$=190.

Intermediate 18: 3-(5-fluoro-2-((2-fluoro-3-(methylsulfonyl)phenyl)amino)pyrimidin-4-yl)-1H-indol-7-amine Step 1

A solution of potassium carbonate (40.9 mL, 678.28 mmol) was charged to a 1 L reactor equipped with a thermometer and nitrogen inlet. The mixture was degassed three times with N$_2$ at room temperature (23° C.). 7-nitro-3-(4,4,5,5-tetramethyl-1,3,2-dioxaborolan-2-yl)-1-tosyl-1H-indole, Intermediate 1 (100 g, 226.09 mmol), 2,4-dichloro-5-fluoropyrimidine (49.1 g, 293.92 mmol) and methyl THF (1000 mL) were added and stirred for 10 min at room temperature. The resulting mixture was degassed 3 times with nitrogen. Dichloro[1,1'-bis(diphenylphosphino)ferrocene]palladium dichloromethane adduct (9.23 g, 11.30 mmol) was added to the reaction mixture and the resulting mixture was degassed and backfilled again (3×N$_2$) and stirred at 23° C. over night to give a yellow precipitate. Heptane (500 mL) was charged to the reaction mixture at room temperature and stirred for 10 min. The stirring was then stopped and the precipitate allowed to settle down. The reaction mixture was cooled to 5° C. and stirred for 1 h. The precipitate was filtered through a Glass-funnel, washed with water until water reached the neutral pH (13 vol, displacement wash, 1.3 L). The filter cake was then washed with EtOAc/heptane mixture 1:1 (5×2 vol, 1 L) at room temperature, heptane (2×200 mL, 2×2 vol) and the solid dried under vacuum at 35° C. over night to afford 3-(2-chloro-5-fluoropyrimidin-4-yl)-7-nitro-1-tosyl-1H-indole (97 g, 89% effective yield). $^1$H NMR (400 MHz, DMSO-$d_6$) δ 2.41 (s, 3H), 7.51 (d, 2H), 7.69 (t, 1H), 7.95 (d, 2H), 8.01 (dd, 1H), 8.75 (d, 1H), 8.81 (dd, 1H), 9.01 (d, 1H). m/z (ES+), [M+H]$^+$=447.2.

Step 2

3-(2-chloro-5-fluoropyrimidin-4-yl)-7-nitro-1-tosyl-1H-indole (89.5 g, 200.30 mmol), 2-fluoro-3-(methylsulfonyl)aniline hydrochloride, Intermediate 2 (54.2 g, 240.36 mmol), Pd$_2$(dba)$_3$ (9.17 g, 10.01 mmol) and 2'-(dicyclohexylphosphino)-N,N-dimethyl-[1,1'-biphenyl]-2-amine (7.88 g, 20.03 mmol) was added to a 2 L reactor under nitrogen. Degassed 2-2-methyltetrahydrofuran (1000 mL) and a solution of cesium carbonate (137 g, 420.62 mmol) in water (450 mL) were added at room temperature and the reaction mixture was degassed (×7). The reaction was then heated to 72.6° C. and then stirred overnight. The reaction was cooled to 4-5° C. and stirred for at least 30 min. The solid was filtered on a Büchner funnel, washed with cold 2-2-methyltetrahydrofuran (300 mL, 3 vol), water (3×300 mL, 3 vol) and EtOAc/heptane mixture 1:2 (3×300 mL, 3 vol) and dried under vacuum at 40° C. to afford 5-fluoro-N-(2-fluoro-3-(methylsulfonyl)phenyl)-4-(7-nitro-1-tosyl-1H-indol-3-yl)pyrimidin-2-amine (77.89 g, 65% effective yield) as a brown solid.

$^1$H NMR (400 MHz, DMSO-$d_6$) δ 2.56-2.64 (m, 3H), 3.42 (d, 3H), 7.52-7.64 (m, 4H), 7.73 (t, 1H), 7.98-8.09 (m, 3H), 8.22 (t, 1H), 8.71 (s, 1H), 8.79 (d, 1H), 8.94 (d, 1H), 9.89 (s, 1H). m/z (ES+), [M+H]$^+$=600.2.

Step 3

5-fluoro-N-(2-fluoro-3-(methylsulfonyl)phenyl)-4-(7-nitro-1-tosyl-1H-indol-3-yl)pyrimidin-2-amine (97.7 g, 129.87 mmol) was charged to a 5 L reactor at room temperature. A mixture of THF (100 mL) and 3.8 M NaOH (aq) (1000 mL) were added to give a brown insoluble mixture. The mixture was heated to 75° C. with reflux and stirred over the weekend. THF (10 vol) and heptane (10 vol) were charged to the reaction mixture. It was then allowed to cool to 17° C. over 40 min, stirred for 60 min and the solid filtered on a Buchner funnel. The filter cake was washed with 1M citric acid (500 mL, until pH neutral), water (5×300 mL, until pH neutral) followed by heptane/EtOAc (4×400 mL). The solid was dried under vacuum to afford 5-fluoro-N-(2-fluoro-3-(methylsulfonyl)phenyl)-4-(7-nitro-1H-indol-3-yl)pyrimidin-2-amine (55.0 g, 95%).

$^1$H NMR (400 MHz, DMSO-$d_6$) δ 3.27-3.38 (m, 3H), 7.30 (t, 1H), 7.47 (t, 1H), 7.64 (t, 1H), 8.11-8.29 (m, 3H), 8.52 (d, 1H), 8.98 (d, 1H), 9.60 (s, 1H), 12.57 (s, 1H). m/z (ES+), [M+H]$^+$=446.2.

Step 4

To as stirred suspension of 5-fluoro-N-(2-fluoro-3-(methylsulfonyl)phenyl)-4-(7-nitro-1H-indol-3-yl)pyrimidin-2-amine (59.5 g, 123.5 mmol, 92.5% Wt) in THF/EtOH 2:1 (600 mL) at room temperature and under nitrogen were added 10% Pd/C (12.0 g, 123.5 mmol, 50% wet) and a solution of ammonium formate (46.8 g, 741.4 mmol) in water (50 mL). The reaction mixture was slowly heated to 70° C. and stirred for 30 min. 12 g activated carbon was added and the mixture was stirred for 15 min. The reaction mixture was cooled to 40° C. and filtered on a Büchner funnel (paper) under nitrogen. The filter cake was washed with THF/EtOH (160 mL). The filtrate was concentrated to 4 vol and resulting slurry cooled to room temperature and filtered under nitrogen. The solid was washed with water (2 vol), ethanol (2 vol) and dried under nitrogen/vacuum at 40° C. to afford 3-(5-fluoro-2-((2-fluoro-3-(methylsulfonyl)phenyl)amino)pyrimidin-4-yl)-1H-indol-7-amine (44.3 g, 86%) as a light brown solid.

$^1$H NMR (400 MHz, DMSO-$d_6$) δ 3.28 (s, 3H), 5.20 (bs, 2H), 6.43 (dd, 1H), 6.78 (t, 1H), 7.44 (t, 1H), 7.57-7.63 (m, 1H), 7.66 (d, 1H), 8.09-8.25 (m, 2H), 8.38 (d, 1H), 9.34 (s, 1H), 11.57 (s, 1H). m/z (ES+), [M+H]$^+$=416.3.

Intermediate 28: methyl 3-methoxy-2-(4-methylpiperazin-1-yl)propanoate 1-methylpiperazine (100 g, 988.4 mmol) and potassium carbonate (164 g, 1186 mmol) were slurried in dry acetonitrile (800 mL) under nitrogen. Methyl 2-bromo-3-methoxypropanoate (201 g, 988.4 mmol) was added to the slurry at 50-60° C. over a period of 40 minutes. The resulting mixture was heated under nitrogen at 61° C. for 23 hours and was then cooled to 20° C. The solid was filtered off. The filtrate was evaporated to an oily residue that was dissolved in 1M HCl (1000 mL). pH was then adjusted to 1 with 4M HCl (~300 mL). The resulting solution was extracted with DCM (200 mL). The water solution was made basic with saturated $Na_2CO_3$ (1000 mL) to pH 9 and extracted with DCM (2×500 mL). pH of the aqueous phase was then raised to 10-11 with sodium hydroxide and extracted with DCM (2×500 mL). The four organic phases were combined and evaporated in vacuo to yield methyl 3-methoxy-2-(4-methylpiperazin-1-yl)propanoate (181 g, 85%).

$^1$H NMR (400 MHz, $CDCl_3$) δ 2.07 (s, 3H), 2.14-2.34 (m, 4H), 2.39-2.52 (m, 4H), 3.14 (s, 3H), 3.22 (dd, 1H), 3.42 (dd, 1H), 3.48-3.56 (m, 4H).

Intermediate 48: Lithium 3-methoxy-2-(4-methylpiperazin-1-yl)propanoate

A solution of lithium hydroxide (0.321 g, 13.39 mmol) in water (5 mL) was added to a solution of methyl 3-methoxy-2-(4-methylpiperazin-1-yl)propanoate, Intermediate 28 (1.93 g, 8.92 mmol) in THF (5 mL). A few drops of MeOH was added until the reaction mixture became clear. The reaction was heated at 40° C. for 24 h. The organics were evaporated in vacuo. The residue diluted with water and lyophilized (×3) to yield lithium 3-methoxy-2-(4-methylpiperazin-1-yl)propanoate, (1.92 g, 103%) as a solid.

$^1$H NMR (500 MHz, $D_2O$) δ 2.06 (s, 3H), 2.48 (bs, 8H), 2.99 (t, 1H), 3.20 (s, 3H), 3.46-3.57 (m, 2H).

Synthesis of Free Base Compound of Formula (Ia)

Lithium 3-methoxy-2-(4-methylpiperazin-1-yl)propanoate, Intermediate 48 (430 mg, 2.06 mmol), 2-(3H-[1,2,3]triazolo[4,5-b]pyridin-3-yl)-1,1,3,3-tetramethylisouronium hexafluorophosphate(V) (785 mg, 2.06 mmol) and DIPEA (1.068 mL, 6.11 mmol) were dissolved in DMF (10 mL) and stirred at room temperature for 5 min and 3-(5-fluoro-2-((2-fluoro-3-(methylsulfonyl)phenyl)amino)pyrimidin-4-yl)-1H-indol-7-amine, Intermediate 18 (635 mg, 1.53 mmol) was then added.

The reaction was stirred at room temperature for 2 h then diluted with DCM (75 mL) and 5% $Na_2CO_3$ (aq) (50 mL), shaken and the phases separated. The aqueous phase was extracted with DCM (2×50 mL). The combined organic phases were dried with a phase separator, filtered and evaporated in vacuo. The compound was purified by preparative HPLC on a XBridge C18 column (10 μm, 250×50 mm) using a gradient of 15-65% acetonitrile in $H_2O$/ACN/$NH_3$ 95/5/0.2 buffer over 20 minutes with a flow of 100 mL/min. The compounds were detected by UV at 220 nm. The product peaks were collected and lyophilized. Then crystallized from acetonitrile and the solid was collected by filtration, washed with minimal amount of acetonitrile and dried in vacuo.

The enantiomers were separated by chiral-SFC on a CelluCoat (250×30 mm, 5 m) column using 25% IPA/DEA 100:0.5 in $CO_2$ at 150 bar with a flow of 140 mL/min. The enantiomers were detected by UV at 270 nm. The first eluting enantiomer was collected and lyophilized to afford N-(3-(5-fluoro-2-((2-fluoro-3-(methylsulfonyl)phenyl)amino)pyrimidin-4-yl)-1H-indol-7-yl)-3-methoxy-2-(4-methylpiperazin-1-yl)propanamide The second eluting enantiomer was collected and lyophilized. The residue was recrystallized by stirring a suspension in EtOH/water (3:1) (5 mL), heated to 70° C. using an oil bath and a seed added. The oil bath temperature was then set to 23° C. and the suspension slowly allowed to attain room temperature. Stirring was continued for 5 days to give a milky like slurry containing short needle shaped crystals with a mix in of longer needle shaped crystals. The suspension was heated to 70° C. with stirring, the heating and stirring was then turned off and the mixture allowed to slowly reach room temperature (2×). Only nice long needle shaped crystals. The suspension was left standing for one more week without stirring. The solid was filtrated off and dried in vacuo at 40° C. to afford (R)—N-(3-(5-fluoro-2-(2-fluoro-3-(methylsulfonyl)phenylamino)pyrimidin-4-yl)-1H-indol-7-yl)-3-methoxy-2-(4-methylpiperazin-1-yl)propanamide (186 mg, 20%, 99.4% ee) as white needle shaped crystals.

$^1$H NMR (500 MHz, DMSO-$d_6$) δ 2.14 (s, 3H), 2.23-2.45 (m, 4H), 2.57-2.67 (m, 2H), 2.69-2.78 (m, 2H), 3.26-3.34 (m, 6H), 3.50 (t, 1H), 3.67 (dd, 1H), 3.79 (dd, 1H), 7.03 (t, 1H), 7.4-7.55 (m, 2H), 7.62 (t, 1H), 8.13-8.33 (m, 3H), 8.44 (d, 1H), 9.46 (s, 1H), 9.84 (s, 1H), 11.48 (s, 1H). $^{19}$F NMR (470 MHz, DMSO-$d_6$) δ−120.52, −147.75. m/z (ES+), [M+H]$^+$=600.5.

Synthesis of Xinafoate Salt of Formula (Ia)

(R)—N-(3-(5-fluoro-2-((2-fluoro-3-(methylsulfonyl)phenyl)amino)pyrimidin-4-yl)-1H-indol-7-yl)-3-methoxy-2-(4-methylpiperazin-1-yl)propanamide (345 g, 563.82 mmol) was charged to the 10 L reactor with ethyl acetate (20 vol) (7 L) and methanol (4 vol) (1.4 L) ("SM solution"). Jacket temp set to 65° C. 1-hydroxy-2-naphthoic acid (106 g, 563.82 mmol) was dissolved in methanol (1.5 vol) (0.7 L) and ethyl acetate (1.5 vol) (0.7 L) in a 2 L reactor and heated to 50° C. The Xinafoic acid solution was polish filtered through a celite to remove insoluble and rinsed with EtOAc/MeOH (2:1, 150 ml). The SM solution was polish filtered through a celite filter and SM crystallized in the receiver vessel due to cooling but not in the filter. Filtration time was 30 min for ~9 L. The SM suspension was recharged to the reactor and heated to 65° C. to redissolve. The Xinafoic acid solution was added to the 20 L reactor with jacket temp set to 70° C. The solution (SM solution+Xinafoic acid solution) was seeded with crystalline material of (R)—N-(3-(5-fluoro-2-((2-fluoro-3-(methylsulfonyl)phenyl)amino)pyrimidin-4-yl)-1H-indol-7-yl)-3-methoxy-2-(4-methylpiperazin-1-yl)propanamide and crystallization initiated instantly. Nitrogen air flow was passed over the headspace to the condenser to distill off MeOH. Ethyl acetate (2 L) was added over 5 min to compensate for loss to azeotrope and ~3 L distilled off. Distillation completed (5 L collected). Cooling ramp started. 75° C. to 10° C. over 600 min then was held at 10° C. The solid was filtered off using a P3 glass sinter funnel. Filtration was very fast. The solid was washed via the reactor with ethyl acetate (2 L) and left to dry under Nitrogen air flow in the funnel. The solid was transferred to a drying vat and dried in a vacuum oven at 40° C.

Mass start: 426 g (4-{(2R)-1-[(3-{5-fluoro-2-[2-fluoro-3-(methanesulfonyl)anilino]pyrimidin-4-yl}-1H-indol-7-yl)amino]-3-methoxy-1-oxopropan-2-yl}-1-methylpiperazin-1-ium; 1-hydroxynaphthalene-2-carboxylate (420 g, 95%) was obtained as an off white crystalline solid.

1H NMR (400 MHz, DMSO) δ 0.97 (s, OH), 1.78 (s, OH), 2.29 (s, 3H), 2.58-3.03 (m, 8H), 3.09 (s, 7H), 3.37-3.72 (m, 3H), 3.83 (s, OH), 6.69-6.97 (m, 2H), 7.11-7.36 (m, 4H), 7.42 (s, 1H), 7.54 (t, 2H), 7.86-8.16 (m, 4H), 8.24 (s, 1H), 9.26 (s, 1H), 9.86 (s, 1H), 11.52 (s, 1H).

For XRPD, the sample was mounted on single silicon crystal (SSC) wafer mount and powder X-ray diffraction was recorded with a Theta-Theta Bruker D8 Advance (wavelength of X-rays 1.5418 Å nickel-filtered Cu radiation, Voltage 40 kV, filament emission 40 mA). 2.5° soller slit and 3 mm antiscatter slit were used and the samples were rotated during measurement. Samples were scanned from 2-50° 2-Theta using a 0.02° step width and a 0.04° s$^{-1}$ time per step measurement time using a LynxEye 3° PSD detector (10.5 mm detector slit).

TABLE 1

| XRPD Peak positions (°2θ) and intensities | |
| --- | --- |
| Angle 2-Theta (°2θ) | Relative Intensity |
| 8.2 | m |
| 8.9 | m |
| 11.2 | m |
| 14.2 | m |
| 15.0 | s |
| 15.3 | s |
| 16.2 | s |
| 17.5 | m |
| 21.0 | s |
| 22.6 | s |
| 23.0 | m |
| 23.7 | m |
| 24.6 | m |
| 26.2 | m |

The following definitions have been used for the relative intensity (%): 25-100%, vs (very strong); 10-25%, s (strong); 3-10%, m (medium); 1-3%, w (weak);

Example 2

From the crystal structure (performed using single crystal X-ray diffraction, SXRD) of the free base compound of Formula (Ia), it was determined that the form was a non-stoichiometric hydrate. This was also further supported by gravimetric vapor sorption analysis (GVS) since a water uptake of 2% w/w was observed at 0-80% relative humidity and that the compound displayed a weight loss of 5% w/w room temperature (RT) to 120° C.

Accordingly, a salt screen was performed and out of 20 counter ions tested, three salts (phosphoric, sulfuric and xinafoic salt) were scaled up (5 g) and further analysis was performed. The phosphoric and sulfuric salts showed less crystallinity compared to the xinafoic salt, and showed weight loss of 3.2% w/w RT–120° C. (sulfuric salt) and 5.4% w/w RT–120° C. (phosphoric salt). There is no gravimetric sorption analysis performed on these two salts, since the showed such unfavored solid state properties compared to the xinafoate and were similar or worse than those of the free base.

The crystal structure (from SXRD) of the xinafoate salt showed that this salt was a 1:1 salt that was not a non-stoichiometric hydrate but an anhydrous form of the free base compound of Formula (Ia). The simulated powder pattern from the SXRD was overlayed by the experimental powder X-Ray diffraction data (PXRD) indicating that the single crystal structure was the same as bulk.

Independently a polymorph screen has shown that the non-stoichiometric hydrate of the free base compound of Formula (Ia) is the most stable form identified under ambient conditions and that the chances of obtaining an anhydrous free form is to be considered very low. Screening was performed at Almac including over 110 solvent and non-solvent based screening experiments. The xinafoate salt was found to be a non-hygroscopic form of the compound of Formula (1a) showing 0.2% w/w absorption between 0-80% relative humidity and showing a weight loss of 0.2% w/w when heating the compound between RT to 120° C., while the free base compound of Formula (Ia) was found to be slightly hygroscopic showing a 1.7% w/w absorption 0-80% relative humidity and displayed a weight loss of 5% w/w from room temperature (RT) to 120° C.

| Specie | Water absorption 0-80% RH (% w/w) | Weight loss RT-120° C. (% w/w) | Crystallinity by PXRD |
|---|---|---|---|
| Free base compound of Formula (Ia) | ~1.7 | ~5 | Highly crystalline |
| Xinafoate salt of compound of Formula (Ia) | ~0.2 | ~0.2 | Highly crystalline |
| Phosphoric salt of compound of Formula (Ia) | No data | ~5.4 | Poor crystallinity |
| Sulphuric salt of compound of Formula (Ia) | No data | ~3.2 | Poor crystallinity |

Example 3

An alternative synthesis of xinafoate salt of Formula (Ia) is further described below:

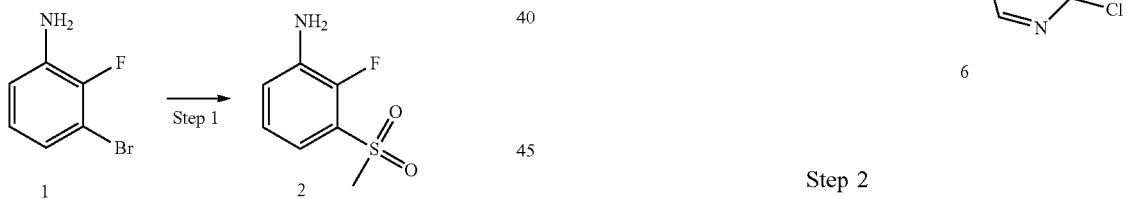

Step 1: 2-fluoro-3-(methylsulfonyl)aniline (2)

To an inertized reactor were added 2-fluoro-3-bromoaniline (1), 930 g, 1 eq., 4.9 mol and sodium methanesulfinate, 3 eq., 1.5 kg followed by DMSO, 5 L. The reactor content was inertized 5 times and stirred for 30 minutes at 20-30° C. Copper(I)iodide, 0.2 eq., 187 g and 1,2-Dimethylethylenediamine, 0.4 eq., 173 g were added to the reactor which then was inertized 3 times. The reaction mixture was stirred at 110-120° C. for 17 hours before it was deemed ready to work up. The mixture was cooled to 20-30° C. and water, 10 L, was added followed by ethyl acetate, 10 L. The mixture was stirred for 30 minutes and the organic layer was separated and the aqueous was extracted twice with ethyl acetate (2×10 L). The combined organics were evaporated to dryness and dissolved in 2 L, ethyl acetate. The crude product solution was filtered through a short silica column and the column was washed with 10 L of a 1:1 mixture of ethyl acetate/petroleum ether. The eluate was then concentrated to 2 L. To this solution was slowly added heptane, 1 L, over 2 hours at 20-30° C. The precipitated product was filtered off and dried at 40-50° C. under reduced pressure to give 0.6 kg, 65% of the desired product.

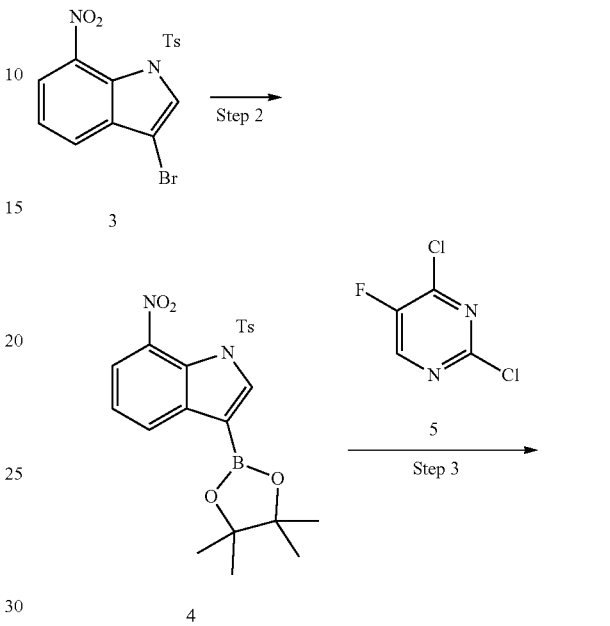

Step 2

7-nitro-3-(4,4,5,5-tetramethyl-1,3,2-dioxaborolan-2-yl)-1-tosyl-1H-indole. (4)

To an inertized reactor was added 3-bromo-7-nitro-1-(p-tolylsulfonyl)indole (3), 1.2 kg, 3 mol and bis(pinacolato)diboran, 1.14 kg, 4.5 mol, 1.5 eq. followed by potassium acetate, 590 g, 6 mol, 2 eq. The reactor content was then inertized and 8.4 L of 1,4-dioxane was charged. The reactor was inertized 3 times followed by the addition of Pd(PPh$_3$)$_4$, 0.01 eq., 35 g. The reaction mixture was heated to 95-100° C. and was stirred for 18 hours. A HPLC sample was taken and the mixture was cooled to 20-30° C. 2-Methyl-THF, 8.4 L and 8.4 L of water was added to the reaction mixture which was then stirred for 30 minutes. The organic layer was separated and washed with 10% sodium chloride (aq), 8.4 L three times. The organic solution was evaporated to dryness and was co-evaporated with acetonitrile, 6 L. Finally 6 L of acetonitrile was added and the mixture was stirred at 20-30° C. for two hours and then cooled to 0-5° C. and stirred for two hours followed by filtration. The filtered off product was dried at 40-50° C. under reduced pressure to give 1 kg (75%) of the desired product (4).

Step 3

3-(2-chloro-5-fluoropyrimidin-4-yl)-7-nitro-1-tosyl-1H-indole. (6)

To an inertized reactor was added 7-nitro-3-(4,4,5,5-tetramethyl-1,3,2-dioxaborolan-2-yl)-1-tosyl-1H-indole, (4), 1 kg, 2.26 mol and 2,4-dichloro-5-fluoropyrimidine (5), 442 g, 1.2 eq., followed by 4 L of 2-MeTHF. A solution of Potassium carbonate, 937 g (3 eq.) in 2 L of water, was charged to the reactor, which was then inertized 5 times. The catalyst, Pd(dppf)Cl$_2$-DCM, 92 g, 0.05 eq (113 mmol) was added to the reactor which then was inertized 3 times and the mixture was stirred at 20-30° C. for 17 hours. A sample for LCMS was taken and 4 L of n-heptane was added to the reactor during two hours at 20-30° C. The precipitate was stirred for an additional 30 minutes before the product was filtered off and was washed with water, 7 L until the filtrate was neutral (pH 7-8). The wet filter cake was slurried in ethyl acetate, 3 L (3 vol) and filtered. Finally the filter cake was washed with 1 L of ethyl actete and was dried at 40-50° C. under reduced pressure to give 0.9 kg (89%) of the desired product (6).

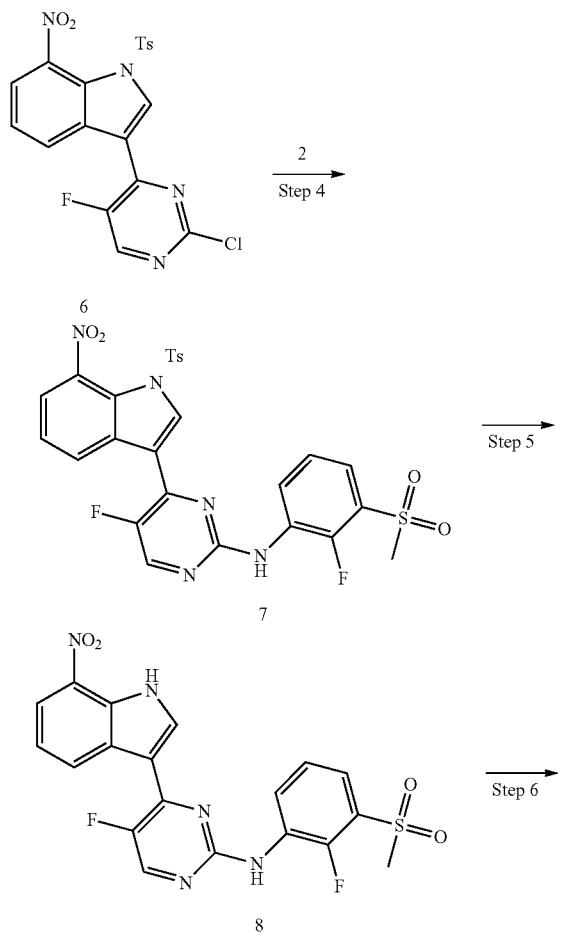

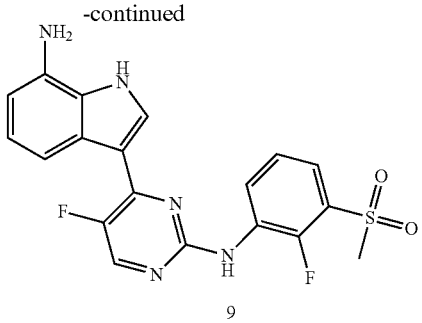

Step 4

5-fluoro-N-(2-fluoro-3-(methylsulfonyl)phenyl)-4-(7-nitro-1-tosyl-1H-indol-3-yl)pyrimidin-2-amine. (7)

To an inertized reactor was added Pd$_2$(dba)$_3$, 124 g (0.05 eq.) and DavePhos, 106 g (0.1 eq.) followed by 2-methyltetrahydrofuran, 3 L. The reactor was inertized 3 times and stirred for 30 minutes at 20-30° C. 3-(2-chloro-5-fluoropyrimidin-4-yl)-7-nitro-1-tosyl-1H-indole (6), 1 eq., 1.2 kg, 2.7 mol, and 2-fluoro-3-(methylsulfonyl)aniline hydrochloride, (2) 1 eq., 610 g, 2.7 mol followed by 2-methyltetrahydrofuran, 3 L were charged to the reactor. Thereafter was added cesium carbonate, 1.1 eq., 970 g in water, 2.4 L to the reactor which then was inertized again 3 times. The reaction mixture was stirred at 75-80° C. for 18 hours when deemed completed. The reaction mixture was cooled to 20-30° C. and the precipitated product was filtered off. The filter cake was washed with 2-methyltetrahydrofuran, 5 L followed by water, 5 L and finally acetone, 5 L. The product was dried at 40-50° C. under reduced pressure to give 1.3 kg of the desired product (7) (80%). $^1$H NMR (400 MHz, DMSO) δ 2.40 (s, 3H), 3.32 (s, 3H), 7.43-7.54 (m, 4H), 7.65 (t, 1H), 7.93 (dd, 3H), 8.13 (t, 1H), 8.57-8.66 (m, 1H), 8.69 (d, 1H), 8.84 (d, 1H), 9.79 (s, 1H).

Step 5

5-fluoro-N-(2-fluoro-3-(methylsulfonyl)phenyl)-4-(7-nitro-1-tosyl-1H-indol-3-yl)pyrimidin-2-amine. (8)

To an inertized reactor was added 5-fluoro-N-(2-fluoro-3-(methylsulfonyl)phenyl)-4-(7-nitro-1-tosyl-1H-indol-3-yl)pyrimidin-2-amine (7), 1.10 kg, 1 eq. 1.84 mol followed by THF, 5.5 L. To the reactor was added 4M NaOH aq. 2.2 L and the resulting mixture was stirred at 65-70° C. for 45 hours whereafter complete hydrolysis was reached. MTBE, 6.6 L, was added over 3 hours with stirring at 15-25° C. resulting in a fine precipitation. The mixture was filtered and the filter cake was washed with water until neutral. Finally the cake was washed with methanol, 2.2 L. The desired product was dried at 40-50° C. under reduced pressure to give 0.70 kg (84%) of the desired product (8). $^1$H NMR (400 MHz, DMSO) δ 3.33 (s, 3H), 7.30 (t, 1H), 7.47 (t, 1H), 7.64 (ddd, 1H), 8.06-8.26 (m, 3H), 8.51 (d, 1H), 8.97 (d, 1H), 9.60 (s, 1H), 12.56 (s, 1H).

Step 6

3-(5-fluoro-2-((2-fluoro-3-(methylsulfonyl)phenyl)amino)pyrimidin-4-yl)-1H-indol-7-amine (9)

To an inertized 25 L reactor preheated to 55 C was charged 5-fluoro-N-(2-fluoro-3-(methylsulfonyl)phenyl)-4-

(7-nitro-1H-indol-3-yl)pyrimidin-2-amine (8) (578 g, 1.26 mol) followed by THF, 8.5 L. To the suspension was added ammonium formiate (475 g, 7.53 mol) in 2.3 L of water followed by of Pd/C (170 g, 80 mmol Pd) and finally 4.3 L of ethanol during 5 minutes. The final mixture was heated from room temperature to 43° C. Reaction was initiated by the addition of ethanol manifested by gas evolution. Within one hour the conversion was complete as monitored by UPLC-MS. The reaction mixture was filtered hot to remove Pd/C. The reactor was rinsed with 3 L of hot THF/ethanol 2:1 (55 C) which was also collected through the the filter. The filtrate was evaporated to a semisolid mixture which was triturated with 2.5 L of ethanol under nitrogen overnight. The product was filtered off and dried at 40° C. in vaccou. Yield: 508 g, assay 100%. M.p.: 236 C (onset DSC), HRMS (ESI+): [M+H]+ m/z calculated for $C_{19}H_{15}F_2N_5O_2S$ 416.0987; Found 416.0996. $^1$H NMR (400 MHz, DMSO) δ 3.29 (s, 3H), 5.20 (s, 2H), 6.44 (d, 1H), 6.79 (t, 1H), 7.45 (t, 1H), 7.56-7.75 (m, 2H), 8.08-8.25 (m, 2H), 8.39 (d, 1H), 9.35 (s, 1H), 11.58 (s, 1H). $^{19}$F NMR (376 MHz, DMSO) δ −147.61, −120.58.

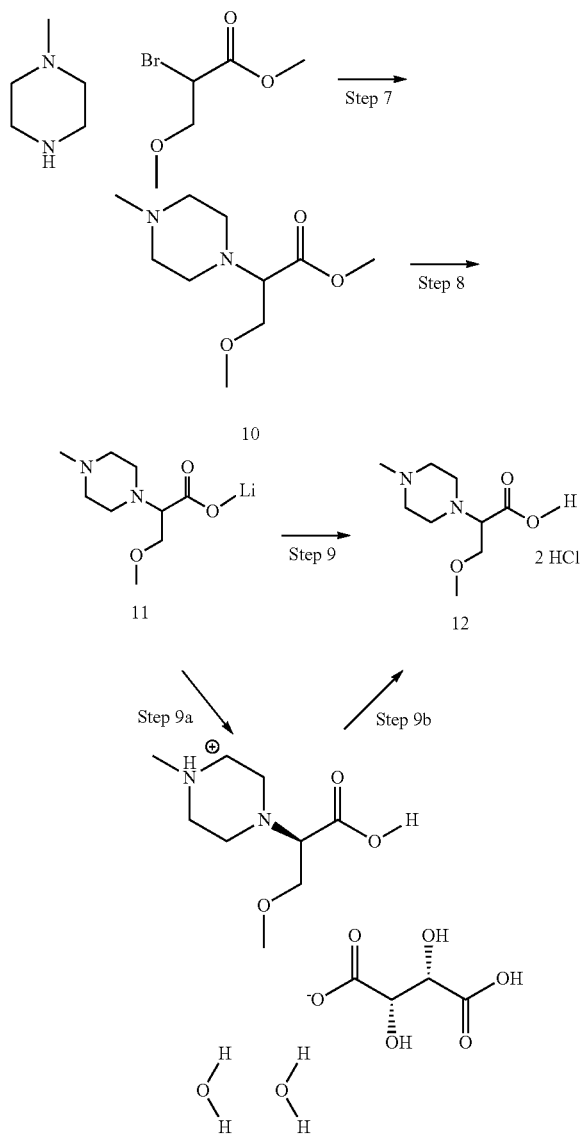

Step 7

Methyl 3-methoxy-2-(4-methylpiperazin-1-yl)propanoate (10)

To a glass reactor under nitrogen was added potassium carbonate, 396 g, 1.3 eq. followed by 1.8 L of dry acetonitrile, Sigma-Aldrich 34851N (0.004% water) and 1-methylpiperazine, 99%, 234 g, 2.3 mol, 1.05 eq. Jacket was set to 60° C. To the resulting slurry was added Methyl 2-bromo-3-methoxypropanoate, 448 g, 97%. 2.2 mol, 300 ml in 200 ml of dry acetonitrile at 60° C. during 1 h, keeping the reaction temperature below reflux. After 19 hours a 99% conversion was established by NMR. The reaction was worked up after 24 h. The reactor content was filtered through a celite dish filter. The filter cake was washed with 500 ml of acetonitrile and the combined organics were evaporated to an oil. The crude product oil was dissolved in 1 L of isopropyl acetate and was extracted with 200 ml of water to remove salts. The product is very soluble in water and back washes with isopropyl acetate is needed to recover material (This water wash can be omitted since it generates a lot of extra work leading only to a marginally improved product purity). The combined isopropyl acetate extracts were evaporated at reduced pressure at 60° C. This yielded the title compound (10) as a yellow oil (471 g, 99% w/w, 98% yield). $^1$H NMR (400 MHz, CDCl$_3$) δ 2.16 (s, 3H), 2.33 (m, 4H), 2.55 (m, 4H), 3.23 (s, 3H), 3.31 (dd, 1H), 3.51 (dd, 1H), 3.60 (dd, 1H), 3.61 (s, 3H). $^{13}$C NMR (101 MHz, CDCl$_3$) δ 45.97, 50.01, 51.32, 55.20, 59.09, 67.03, 70.71, 170.85. HRMS (ESI+): [M+H]+m/z calc'd for $C_{10}H_{21}N_2O_3$ 217.1552; Found 217.1547.

Step 8

Lithium 3-methoxy-2-(4-methylpiperazin-1-yl)propanoate (11)

To a solution of 87 g LiOHxH$_2$O (98%), 1.07 eq. in 1 L of pure water in a 5 L reactor under nitrogen was added a solution of methyl 3-methoxy-2-(4-methylpiperazin-1-yl) propanoate (441 g, 2000 mmol) in 1 L of THF and 300 ml methanol. The reaction mixture was heated at 40° C. for 72 h, whereafter full conversion was established by NMR. The reaction mixture was evaporated to an oil that solidified as a foam after drying in vaccuo at 40° C. to give the title compound (11) (435 g, 97% w/w, 93% yield). $^1$H NMR (400 MHz, CDCl$_3$) δ 2.24 (s, 3H), 2.45 (m, 4H), 2.64 (m, 4H), 3.02 (dd, 1H), 3.63 (dd, 1H), 3.72 (dd, 1H). $^{13}$C NMR (101 MHz, DMSO) δ 45.9, 49.76, 55.01, 57.91, 70.18, 72.18. HRMS (ESI+): [M$_{acid}$+H]+ m/z calc'd for $C_9H_{19}N_2O_3$ 203.1396; Found 203.1388.

Step 9

Chromatography

The enantiomers of 11 (180 g, 865 mmol) were separated by chiral supercritical fluid chromatography, using a Lux Cellulose-4 (5 m, 250×50 mm) with a mobile phase of 25% MeOH/NH3 100/0.5 in CO$_2$, at 120 bar at 30° C., with a flow of 420 g/min and detection at 215 nm. The second eluted compound was collected and evaporated to yield (R)-3-methoxy-2-(4-methylpiperazin-1-yl)propanoic acid of the title compound (80 g, 99.6% ee).

Step 9a

Salt Resolution

L-(+)-Tartaric acid salt of (R)-3-methoxy-2-(4-methylpiperazin-1-yl)propanoic acid Under nitrogen in a stirred reactor lithium 3-methoxy-2-(4-methylpiperazin-1-yl)propanoate, 208 g, 1 mol, was dissolved in 625 ml of distilled water and pH was adjusted to 4 with 3.8M HCl, 340 ml. Temperature rose from ambient to 33° C. L-(+)-Tartaric acid, 145 g, 0.97 mol, was dissolved in 170 ml of distilled water and was added to the previous solution followed by 300 ml of ethanol (99.5% w/w). Crystallisation could be induced by seeding but stirring over night at room temperature (20-21° C.) also induced the crystallization. Prior to filtration, 200 ml of ethanol (99.5% w/w) was slowly added and the reaction mixture was cooled to 10° C. and stirring was continued for 1 h. Product was filtered off and was washed with 300 ml of cold ethanol (99.5% w/w). The collected product crystals were dried in vaccou at 40° C. for 72 h. Yield 144 g, Mw=388.37 (2 crystal water according to x-ray crystal structure analysis), 0.37 mol, 74%. m.p. 139° C. (peak, DSC).). $^1$H NMR (400 MHz, D$_2$O) δ 2.98 (s, 3H), δ 2.84 (s, 3H), δ 3.45-3.71 (m, 8H), δ 3.84 (t, 1H), δ 3.92 (dd, 2H), δ 4.53 (s, 4H), δ 4.79 (s, 4H)+additional water from solvent.

Crystal Data. $C_{13}H_{28}N_2O_{11}$, $M_r$=388.37, orthorhombic, P2$_1$2$_1$2$_1$ (No. 19), a=7.1515(4) Å, b=13.9607(7) Å, c=17.6138(11) Å, α=β=γ=90, V=1758.56(17) Å$^3$, T=100(2) K, Z=4, Z'=1, μ(CuK$_α$)=1.109, 10608 reflections measured, 3096 unique ($R_{int}$=0.0898) which were used in all calculations. The final wR$_2$ was 0.2209 (all data) and R1 was 0.0670 (I>2(I)).

Step 9b

(R)-3-methoxy-2-(4-methylpiperazin-1-yl)propanoic acid bis hydrochloric acid salt (12)

40 g of L-(+)-tartaric acid salt of (R)-3-methoxy-2-(4-methylpiperazin-1-yl)propanoicacid was dissolved in 200 ml of warm distilled water and was loaded on 300 ml of Dowex 50WX2-100 cationic ion exchange resin in a column, approx. 200 g in its H-form (washed to neutral with distilled water). The column was eluted with distilled water (~700 ml, 2-3 column volumes) until it was completely neutral after addition. The amino acid was then eluted with 2M HCl 900 ml (3 column volumes) to give 28 g, 90% (dry weight) of amino acid HCl salt as an oil that soon crystallized. Some material might still be on the column since there was no detector coupled to the ion exchange. NMR. Assay 93%, water content 2.24% (KF). 21 g of product was dissolved in 5 vol. of refluxing abs. ethanol (if material is non-crystalline 3 vol. is enough.), 100 ml and was left to cool to ambient temperature. When crystallization had come to an end 3 vol. of MTBE, 60 ml, was added slowly to decrease the solubility of the salt. The product was filtered of and was dried at 40° C. under reduced pressure for 17 h. Melting point, 141.6 (DSC, onset, 3 C/min). Water content, 6.12% (6.18% one crystal water molecule) NMR assay, 97.5%. Yield, 70%, 14 g. The salt has a solubility in ethanol that makes it not a perfect solvent for the recryst, however adds the water to the salt. Mother liquor contains the missing 30%, which can be recovered. $^1$H NMR (400 MHz, D$_2$O) δ 2.99 (s, 3H), δ 3.33 (s, 3H), δ 3.53 (t, 2H), δ 3.66 (m, 2H), δ 3.85 (t, 2H), δ 3.96 (m, 1), δ 3.98 (d, 2H), δ 4.32 (t, 1H), δ 4.79 (s, 2H)+additional water from solvent.

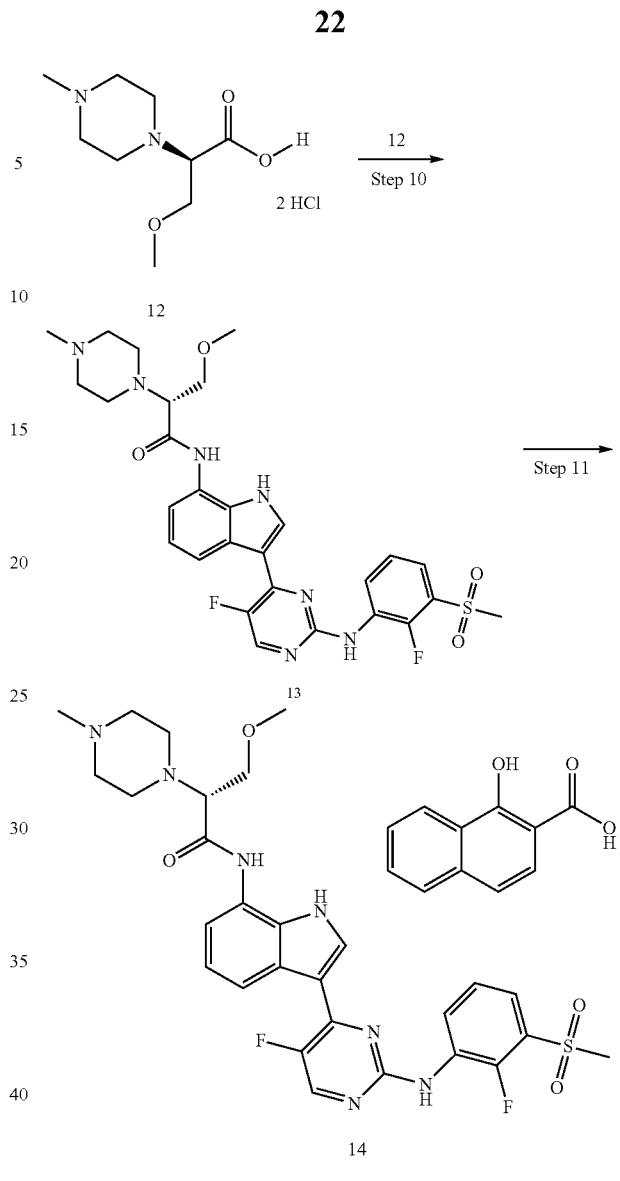

Step 10

(R)—N-(3-(5-fluoro-2-((2-fluoro-3-(methylsulfonyl) phenyl)amino)pyrimidin-4-yl)-1H-indol-7-yl)-3-methoxy-2-(4-methylpiperazin-1-yl)propanamide (13)

To a 10 L inertized cryo reactor at room temperature was charged (R)-3-methoxy-2-(4-methylpiperazin-1-yl)propanoic acid, 2HCl (12) (430 g, 1187.6 mmol) followed by 3 L of DMF (6 vol). To the light brown solution was charged 3-(5-fluoro-2-((2-fluoro-3-(methylsulfonyl)phenyl)amino) pyrimidin-4-yl)-1H-indol-7-amine (9) (449 g, 1079.6 mmol). The resulting dark brown clear solution was cooled to −20° C. (jacket was set to −30° C.). Pyridine, 1.3 L, was added during 5 minutes to the reactor. No significant exotherm observed. At −20° C. propane phosphonic acid anhydride (T3P) in DMF (1.9 L, 3239 mmol) was added very slowly not exceeding −13° C. Jacket was set to −40° C. due to the exothermic reaction. The addition was finished after 75 minutes. After ⅔ of the addition a sample was taken and an SFC-MS was run, almost complete conversion. Complete conversion after full addition. Final analysis UPLC-MS. The reaction mixture was quenched by a slow addition of water at −15° C. during 1 h. The quenched mixture was stirred for an additional 30 min at −15° C. In a larger reactor, 8.5% NaHCO$_3$(14 L) was prepared in advance and cooled to +5° C., to minimize the foam generation the cold quenched reaction mixture was transferred slowly to the reactor containing 8.5% NaHCO$_3$(14 L) by a short tube applying under pressure. After a one hour addition an additional 18 L of saturated bicarbonate solution was added whereby the product started to precipitate from the clear solution. The precipitated product mixture was stirred for 30 min at +5° C. The crude clay-like product was filtered off. The product filtered poorly and the procedure took considerable time to perform. The product was dried at 40° C. under reduced pressure for 72 h. Yield 665 g with an assay of 87% (81%).

The dry crude material 665 g with assay 87%, was charged to an inertized reactor and 13 L of acetonitrile was added. The mixture was stirred at reflux with start from ambient. Acetonitrile, 2 L, was added to improve the solubility of the product. The not clear solution was clear filtered whereby some crystallisation was initiated. The filtration was difficult and not soluble material clogged the filter. Product solution in the filter had to be returned to the reactor when clogging occurred. In all, the volume was doubled during the filtration which took long time. The clear filtered organics was transferred to another reactor and the volume was reduced to 13 L. A crystallisation was initiated from reflux (clear solution) with slow cooling to 5° C. during 24 h. The product was filtered off and was washed with 2 vol. cold acetonitrile. The product was dried under reduced pressure over night at 40° C. Yield: 364 g, 63%, purity 98% (NMR)

HRMS (ESI$^+$): [M+H]+m/z calc'd for C$_{28}$H$_{31}$F$_2$N$_7$O$_4$S 600.2204; Found 600.2199. $^1$H NMR (400 MHz, DMSO) δ 2.14 (s, 3H), 2.35 (s, 4H), 2.55-2.68 (m, 2H), 2.68-2.85 (m, 2H), 3.29 (s, 3H), 3.30 (s, 3H), 3.51 (t, 1H), 3.67 (dd, 1H), 3.79 (dd, 1H), 7.04 (t, 1H), 7.39-7.57 (m, 2H), 7.62 (td, 1H), 8.11-8.33 (m, 3H), 8.44 (d, 1H), 9.46 (s, 1H), 9.88 (s, 1H), 11.53 (s, 1H).

Step 11

(R)—N-(3-(5-fluoro-2-((2-fluoro-3-(methylsulfonyl)phenyl)amino)pyrimidin-4-yl)-1H-indol-7-yl)-3-methoxy-2-(4-methylpiperazin-1-yl)propanamide xinafoic acid salt (14)

(R)—N-(3-(5-fluoro-2-((2-fluoro-3-(methylsulfonyl)phenyl)amino)pyrimidin-4-yl)-1H-indol-7-yl)-3-methoxy-2-(4-methylpiperazin-1-yl)propanamide (13) (345 g, 563.82 mmol) was charged to a inertized 10 L reactor. ethyl acetate (7 L, 20 vol) and methanol (1.4 L, 4 vol) was charged. The mixture was heated to 65° C. until all had dissolved. The solution was polish filtered hot through a celite filter. Crystallization occurred in the filtrate. The slurry filtrate was transferred back to the reactor and heated to 60° C. until fully redissolved. 1-hydroxy-2-naphthoic acid (106 g, 563.82 mmol) was charged to a inertized 2 L reactor. Methanol (0.7 L, 1.5 vol) and ethyl acetate (0.7 L, 1.5 vol) was charged and the mixture was heated to 50° C. until all had dissolved. The solution was polish filtered and the filter was rinsed with EtOAc/MeOH (2:1, 150 ml). The resulting solution was added to the 10 L reactor at 60° C. giving a clear solution which was stirred for 10 min. The solution was seeded with crystalline material (7 g) from a previous batch. Crystallization initiates instantly. Solvent was distilled off at ambient pressure and 75° C. jacket temperature with the aid of a nitrogen flow over the headspace until the reflux temperature was above 70° C. 5 L distillate was collected and EtOAc (2 L) was added to the reactor to compensate the volume loss. The reactor was slowly cooled to 10° C. over 10 h and kept at that temperature for 4 h. The solid was filtered off and was washed via the reactor with ethyl acetate (2 L). The solid was dried under vacuum at 40° C. (R)—N-(3-(5-fluoro-2-((2-fluoro-3-(methylsulfonyl)phenyl)amino)pyrimidin-4-yl)-1H-indol-7-yl)-3-methoxy-2-(4-methylpiperazin-1-yl)propanamide xinafoic acid salt (14) (420 g, yield 95%) was obtained as an off-white crystalline solid. Purity (NMR) 97.7%

1H NMR (400 MHz, DMSO) δ 2.29 (s, 3H), 2.58-3.03 (m, 8H), 3.09 (s, 7H), 3.37-3.72 (m, 3H), 6.69-6.97 (m, 2H), 7.11-7.36 (m, 4H), 7.42 (s, 1H), 7.54 (t, 2H), 7.86-8.16 (m, 4H), 8.24 (s, 1H), 9.26 (s, 1H), 9.86 (s, 1H), 11.52 (s, 1H). 19F NMR (376 MHz, DMSO) δ −147.71, −120.45. Melting point: 189° C. (DSC, peak)

HRMS (ESI$^+$): [M+H]$^+$ m/z calc'd for C$_{28}$H$_{31}$F$_2$N$_7$O$_4$S, 600.2204; Found 600.2199 (Parent)

The invention claimed is:

1. A xinafoate salt of Formula (Ia):

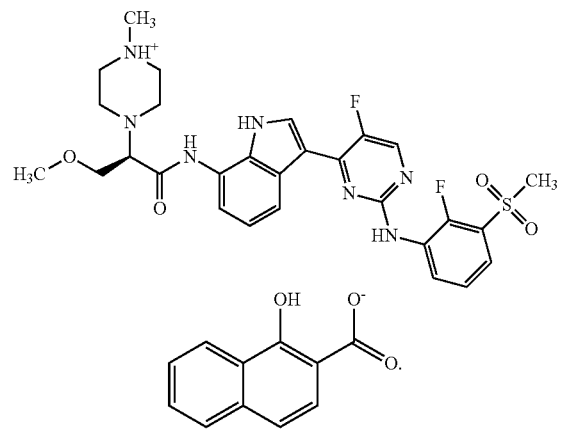

Formula (Ia)

2. The salt according to claim 1, which is in crystalline form.

3. A pharmaceutically acceptable composition comprising a xinafoate salt of claim 1, in association with a pharmaceutically-acceptable excipient, diluent or carrier.

4. A pharmaceutically acceptable composition comprising a xinafoate salt of claim 2, in association with a pharmaceutically-acceptable excipient, diluent or carrier.

5. The salt according to claim 1, which is in crystalline Form A wherein crystalline Form A has an X-ray powder diffraction pattern with specific peaks at about 2θ measured using CuKα radiation 15.0° and 21.0° and 22.6° (±0.1°).

6. The salt according to claim 5, wherein crystalline Form A has an X-ray powder diffraction pattern with specific peaks at about 2θ measured using CuKα radiation 8.2, 8.9, 11.2, 14.2, 15.0, 15.3, 16.2, 17.5, 21.0, 22.6, 23.0, 23.7, 24.6 and 26.2° (±0.1°).

7. A process for the preparation of a xinafoate salt of claim 1 comprising:
(i) Dissolving (R)—N-(3-(5-fluoro-2-(2-fluoro-3-(methylsulfonyl)phenylamino)pyrimidin-4-yl)-1H-indol-7-yl)-3-methoxy-2-(4-methylpiperazin-1-yl)propanamide free base in a suitable solvent;

(ii) Dissolving xinafoate acid in a suitable solvent;
(iii) Mixing the two solutions;
(iv) Crystallising the xinafoate salt of (R)—N-(3-(5-fluoro-2-(2-fluoro-3-(methylsulfonyl)phenylamino)pyrimidin-4-yl)-1H-indol-7-yl)-3-methoxy-2-(4-methylpiperazin-1-yl)propanamide; and
(v) Isolating the xinafoate salt of (R)—N-(3-(5-fluoro-2-(2-fluoro-3-(methylsulfonyl)phenylamino)pyrimidin-4-yl)-1H-indol-7-yl)-3-methoxy-2-(4-methylpiperazin-1-yl)propanamide.

8. A method of treating a JAK kinase mediated disease selected from asthma or COPD in a subject in need thereof, comprising administering to the subject an effective amount of a xinafoate salt of Formula (Ia) according to claim 1.

9. The method of claim 8, wherein the JAK kinase mediated disease is asthma.

10. A method of treating JAK kinase mediated disease selected from asthma or COPD in a subject in need thereof, comprising administering to the subject an effective amount of crystalline Form A of Formula (Ia) according to claim 5.

11. The method of claim 10, wherein the JAK kinase mediated disease is asthma.

12. The process of claim 7, further comprising:
adding seed crystals of the xinafoate salt of (R)—N-(3-(5-fluoro-2-(2-fluoro-3-(methylsulfonyl)phenylamino)pyrimidin-4-yl)-1H-indol-7-yl)-3-methoxy-2-(4-methylpiperazin-1-yl)propanamide,
after mixing the two solutions and before crystallising the xinafoate salt of (R)—N-(3-(5-fluoro-2-(2-fluoro-3-(methylsulfonyl)phenylamino)pyrimidin-4-yl)-1H-indol-7-yl)-3-methoxy-2-(4-methylpiperazin-1-yl)propanamide.

* * * * *